United States Patent [19]

Hiatt

[11] Patent Number: 4,600,559
[45] Date of Patent: Jul. 15, 1986

[54] VACUUM EXTRACTOR WITH CRYOGENIC CONCENTRATION AND CAPILLARY INTERFACE

[75] Inventor: Michael H. Hiatt, Las Vegas, Nev.

[73] Assignee: The United States of America as represented by the Administrator Environmental Protection Agency, Washington, D.C.

[21] Appl. No.: 362,379

[22] Filed: Mar. 26, 1982

[51] Int. Cl.⁴ ............................................. G01H 30/02
[52] U.S. Cl. ...................................... 422/89; 422/240
[58] Field of Search ........................ 422/89, 78, 80, 81, 422/240; 436/20, 161, 177, 181; 203/49, 91; 202/205, 182; 73/23.1

[56] References Cited

U.S. PATENT DOCUMENTS

| | | | |
|---|---|---|---|
| 2,600,158 | 6/1952 | Clothier | 436/181 |
| 4,003,257 | 1/1977 | Fletcher | 422/89 |
| 4,133,640 | 1/1979 | Clinton et al. | 436/161 |
| 4,273,742 | 6/1981 | Huber et al. | 422/81 |
| 4,314,824 | 2/1982 | Hansen et al. | 422/81 |

FOREIGN PATENT DOCUMENTS

| | | | |
|---|---|---|---|
| 173752 | 10/1982 | Japan | 422/89 |
| 811143 | 3/1981 | U.S.S.R. | 436/161 |

*Primary Examiner*—Hiram H. Bernstein

[57] ABSTRACT

An apparatus and process for the vacuum distillation of volatile organic pollutants contained in various environmental sample matrices, such as sediments, soils, water and fish is connected to a cryogenic concentrating means. The volatile organic pollutants in the sample are first separated from the water vapors in the mixture which emanates from a sample chamber by condensing the water vapors in a precooling trap. The volatile organic compounds are first condensed in a cryogenic concentration trap which is subsequently warmed to transfer the volatile organic vapors to a cryogenic focusing trap cooled to −196° C. A series of manually activated or automatically solenoid activated valves controls passage of the various fluids through a conduit network selectively connecting the various cooling traps and the outlet of a sample chamber to one another. A cooled pump oil trap may be connected into the conduit network to condense pump oil vapors and thus prevent pump oil contamination of the apparatus. A water sample or internal standards inlet is selectively connected by valve actuation to the outlet of the sample chamber. A carrier gas inlet and carrier gas and volatile extract outlet are respectively connected to the outlet of the cryogenic focusing trap by each of a set of 6-port valves. When the organic condensate in the cryogenic focusing trap is heated vapors of the volatile organic pollutants can be entrained within the carrier gas introduced from the inlet port and can be exited from the outlet port for qualitative or quantitative analysis by a gas chromatograph/mass spectrometer or gas chromatograph device which is interfaced by means of a capillary column with the cryogen condensing apparatus. The apparatus is particularly useful in monitoring pollutants in sediments, soils and in fish samples.

6 Claims, 5 Drawing Figures

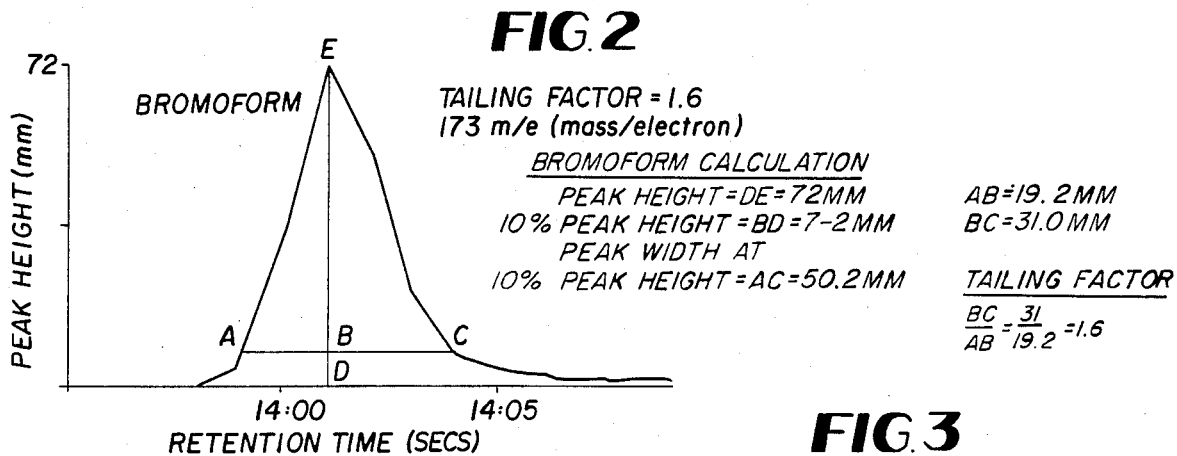
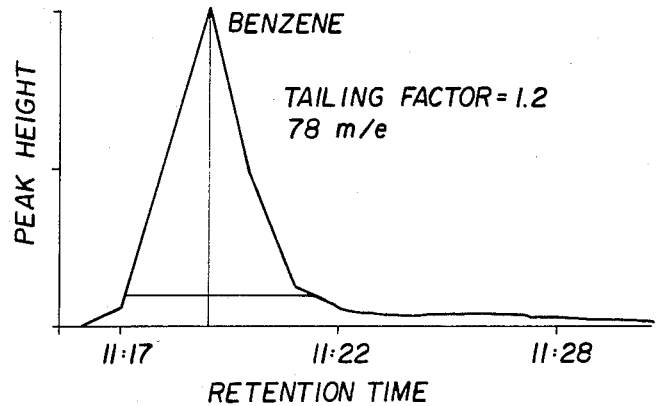
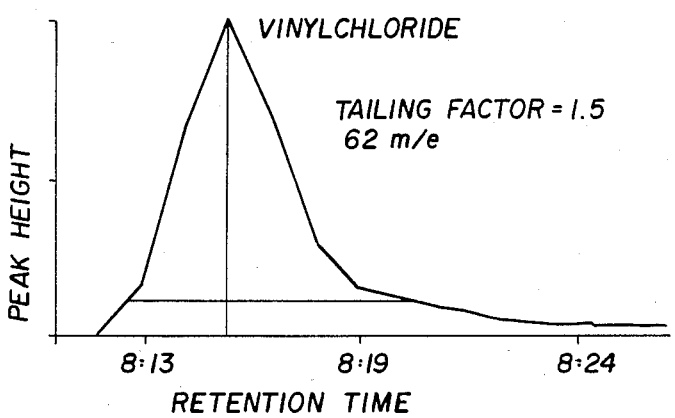
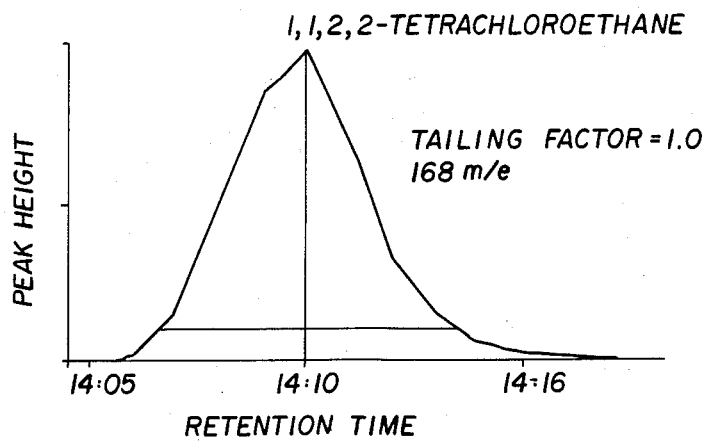

VACUUM EXTRACTOR WITH CRYOGENIC CONCENTRATION AND CAPILLARY INTERFACE

FIELD OF THE INVENTION

The invention relates to a vacuum extraction and cryogenic concentration apparatus for qualitatively or quantitatively analyzing volatile or purgeable chemicals in various environmental sample matrices. The apparatus of the invention can be interfaced with a capillary column chromatography device, such as a gas chromatograph/mass spectrometer, for separation of volatile pollutants extracted from sediments, soils, water and fish.

BACKGROUND OF THE INVENTION

The U.S. Environmental Protection Agency's (EPA'S) water quality and hazardous wastes monitoring programs require quantitative analysis of a variety of environmental samples for volatile organic pollutant compounds. Determination of the volatile priority pollutants in water samples is usually satisfactorily accomplished by practicing EPA-recommended methods. However, the EPA-recommended precedures for the determination of volatile priority pollutants in soils, sediments and fish produce unacceptable results, as evidenced by low spike recoveries and high detection limits. Improved procedures have therefore been sought for effectively carrying out environmental monitoring programs with respect to solid samples of environmental matter.

The vaporization of volatile organic compounds from a sample under vacuum and the subsequent condensation of such compounds in a super-cooled trap seemed to offer some advantageous possibilities in such monitoring procedures since cryogenic concentration has been used successfully for the determination of tritiated methane and the radioisotopes of krypton and xenon. Accordingly, the use of cryogenic concentration appeared to be applicable for quantitatively determining the presence of volatile organic compounds in solid matrices. Vacuum extraction, moreover, was of advantage, in not requiring elevated temperatures or the addition of reagents which could produce unwanted contaminative byproducts due to sample degradation.

Having in mind the above factors, a particular method, known to the art as the purge-and-trap technique, for monitoring solid samples has been developed. In this method, volatile organic compounds are vaporized from the fish or soil sediment matrix under vacuum conditions and the vapors are condensed in a purging trap cooled by liquid nitrogen. The purging trap is transferred to a conventional purge and trap device where the concentrate is treated as a water sample and is analyzed by a Method 624 in the Federal Register 1979 (44FR 69532) developed by T. A. Bellar and J. J. Lichtenberg. Using this method of analysis, the average recovery of volatile organic compounds from samples spiked at the 25 mg/kg level was found to be 94% for sediments and 74% for fish tissue. An inherent problem encountered in the use of the purge-and-trap technique is that water vapor is carried along with the volatile organic compounds and this water interferes with the chromatographic analysis. Moreover, large amounts of carrier gas are needed to purge the volatile compounds. A jet separator or other carrier splitting device is then needed to remove most of the carrier gas. This results in the partial losses of the volatile compounds which limits sensitivity of the analysis.

In one modified purge-and-trap technique, developed by Joe Blazevich, a solid or biological sample is diluted with water and the resulting slurry is treated and analyzed as if it were an ordinary water sample. However, this process results in the foaming of the sample and in uncontrolled variable purging efficiencies.

Another modified purge-and-trap technique, developed by David Speis, uses steam distillation to separate the volatile compounds. The steal-carrier gas mixture is then passed through 5 ml. of water which serves as a conventional trap. However, the steam distillation may generate unwanted by-products due to the decomposition of labile components of the sample by heat, and some of the compounds of interest to the analysis may be lost due to chemical reaction or decomposition.

It is therefore evident from the above methods of analytically determining the volatile compounds in solid soil and biological environmental samples, certain disadvantages arise in reproducibly removing and concentrating the volatile organics for physicochemical determinations.

Since water has been routinely removed from molecular sieves using heat and vacuum and since it is known, as set forth above, that volatile compounds can be collected in a trap cooled with liquid nitrogen, it would appear that a combination of these techniques, with required modifications, could advantageously be used to remove and concentrate volatile organic compounds from a variety of matrices, such as the soil and biological samples, mentioned above.

Accordingly, the invention herein has been developed for the purpose of achieving the purposes set forth above without encountering the problems and disadvantages which have been described supra.

SUMMARY AND OBJECTS OF THE INVENTION

The invention herein comprises a vacuum extractor and cryogenic concentrator interfaced with a capillary column gas chromatograph/mass spectrometer or a gas chromatograph, hereinafter termed a VECCCI for qualitative and quantitative determinations of volatile organic or inorganic compounds in various environmental samples, particularly in solid sediment or biological matrices, such as fish samples.

The VECCCI minimizes the effect of sample matrices on collection of volatile compounds by always producing an extract which contains only those compounds more volatile than water. Numerous sample types can be analyzed consecutively without sample matrix effects. This invention will be useful to all parts of the EPA, other agencies, and the public which are engaged in the qualitative and quantitative determination of volatile pollutants. This apparatus will also be useful in other fields where volatile organic or inorganic compounds need to be concentrated and analyzed at ppb concentrations. This system may be used in forensic chemistry for analysis of air, specimens or other samples for identification of volatiles such as perfume components, alcohol, anesthetics, and flammables. Other practical applications would be isolation and identification of organic or inorganic reactants and intermediates which are trapped during or after a chemical reaction has taken place; isolation and identification of volatile products generated during bioprocesses (e.g., from microorganisms) and the likes.

Accordingly, it is an object of the invention to provide an effective and efficient process for conducting qualitative and quantitative determinations of volatile or purgeable compounds in a variety of solid environmental samples.

Another object of the invention is to utilize a volatile compound analysis system which can be interfaced with a capillary column chromatography device.

Another object of the invention is to utilize a novel means for transferring volatile components from the sample matrix to the vapor phase as opposed to the current usage of "gas stripping" at atmospheric pressure.

Another object is to develop a system for analyzing volatiles in environmental systems other than water.

Still another object of the invention will allow precise environmental determinations of volatile organic or inorganic pollutants at detection levels not attainable with present methods, without an increase in analysis time or expense compared to methods presently in use.

BRIEF DESCRIPTION OF THE DRAWINGS

The description of the invention, which follows, will be more easily understood when read in conjunction with the following figures of the drawing, wherein:

FIG. 2 is a graphic illustration of a peak shape for a volatile bromoform pollutant from which the tailoring factor may be calculated by utilizing a mathematical formula, which will be more fully explained below.

FIG. 3 shows a peak shape for a volatile benzene pollutant obtained by plotting peak height against retention time in a manner similar to that applied in FIG. 2;

FIG. 4 shows a peak shape for a volatile vinyl chloride pollutant obtained in a manner similar to that applied in FIGS. 2 and 3; and FIG. 5 shows a peak shape for a volatile 1,1,2,2-tetra chloroethane pollutant obtained in a manner similar to that applied in the foregoing FIGS. 2 to 4.

DETAILED DESCRIPTION OF THE PREFERRED EMBODIMENTS

Figure 1:
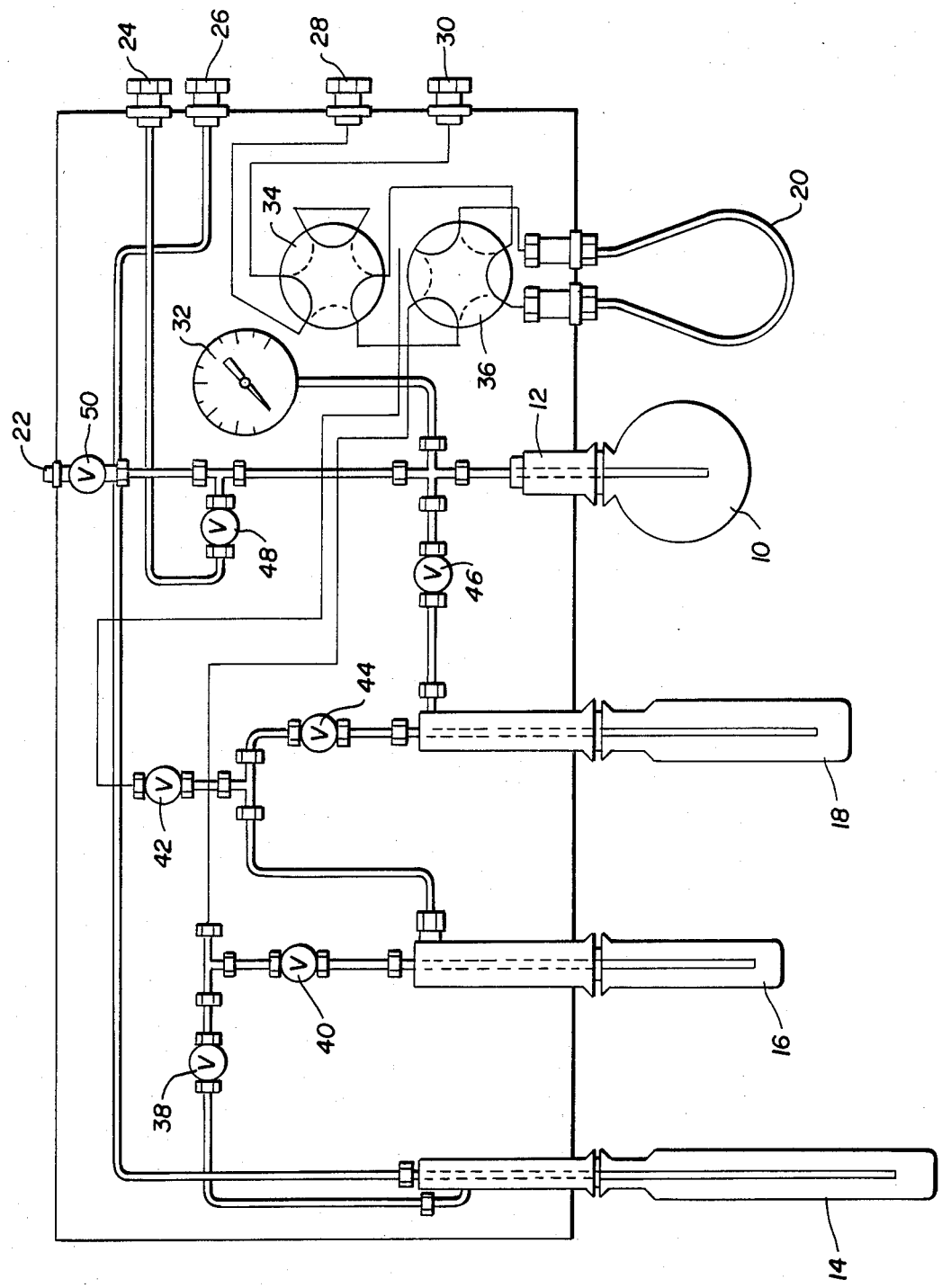
FIG. 1 is a side view in elevation of the novel analytical system of the invention.

The VECCCI was developed for the determination of volatile organic pollutants in various environmental samples, such as water sediment, soil and biological samples, such as fish and other seafood.

In the apparatus of the invention, as shown in FIG. 1, a vacuum imposed through port 26 serves to desorb the volatile organic compounds from the sample material contained in a 100 ml. sample chamber 10. The desorption is assisted by sonic agitation of the sample during evacuation. The vapors (consisting of volatile organics and water) desorbed from the sample pass through a precooling trap 18 which is cooled to a temperature range between −10° C. and −40° C. (to condense water vapors) and then through a second cryogenic concentration trap 16, which has been cooled to −196° C. (to condense the volatile organic compounds). After completion of the vacuum desorption step the trap containing the trapped volatile compounds is warmed and the volatiles are transferred to a stainless steel capillary trap, cooled to −196° C. where the volatile compounds recondense. From this last trap the concentrate is transferred using carrier gas through a valve system to the analyzing instrument for quantitation.

The present prototype of the invention as described below is a manual device. However, this system can easily be automated by using solenoid valves in place of the present manual valves. A subambient circulating bath, which is available commercially, can be used to cool the precooling trap to the desired temperatures. The bath can be transferred to the precool trap bath when needed and then diverted after the analysis using gravity and solenoid valves. Liquid nitrogen can be introduced to the traps which are to be cooled to −196° C. by using the liquid nitrogen dewar cylinder and solenoid valves for input and drainage. Heating filaments can be used for warming the traps during transfer and preparation for the next analysis. A programmable microprocessor can be installed to activate the solenoid valves when called for by the procedure being used. Temperature controllers can be used to maintain proper temperatures in the VECCCI box.

The 100 ml. sample chamber flask 10 is attached with an O-ring and clamp to the VECCCI device. Internal standards and/or sample spikes are introduced through the water sample inlet controlled by a valve 50. The volatile compounds are evacuated from the 100 ml sample flask and recondensed in the extraction cryogen concentration trap 16. Water is condensed in the precooling trap 18, as stated supra; valves 38, 40, 44 and 46 are opened during this transfer operation.

After the extraction operation is completed, valves 40 and 44 are closed and the extraction cryogenic focusing trap 20 is cooled in liquid nitrogen the 6-port valve 36 is put into position to permit fluid access to the cryogenic concentration trap and the cryogenic focusing trap and 6-port valve 34 is put in the rig bypass position. Valve 42 is opened, and trap 16 is warmed causing the extract to be evacuated from trap 16 and recondensed in trap 20. After the volatile compounds have been transferred to trap 20, the six-port valve 36 is switched to the cryogenic focusing trap to capillary position. Then 6-port valve 34 is switched to the rig to capillary position. The trap 20 is then heated and carrier gas entering through inlet 28 transfers the volatile extract to the analytical device, namely the gas chromatograph/mass spectrometer (GC/MS).

The system is decontaminated between runs by removing trap 18 and replacing it with a clean dry trap. Valve 44 may optionally be closed to allow heating of trap 18 and evacuation of the trapped water during the transfer of the volatile compounds from trap 16 to trap 20. Trap 16 is decontaminated by evacuation while the volatile extract is being transferred to the analytical device (i.e. GC/MS). Trap 20 is decontaminated by evacuation and heating while the next sample is being extracted (100-ml flask to 16). While decontaminating trap 20 the 6-port valve 36 is in the evacuation position and the 6-port valve 34 is in the rig bypass position.

Valve 48 is connected to a helium source and is used for pressure-leak testing. Valve 38 is used for isolating the VECCCI for pressure-leak testing.

The pump oil trap 14 is immersed in liquid nitrogen and is used to condense pump oil vapors and thus prevents pump oil contamination of the VECCCI.

A vacuum pressure gauge 32 is connected into the system for monitoring the pressure at valve 46 and at the outlet from sample flask 10. Connected to 6-port valve 34 is a carrier gas inlet 28 and a carrier gas and volatile extract outlet 30. The outlet 30 is connected, via a transfer line, to a capillary column leading to the analytical device. A helium gas inlet 24 is connected to a point of entry into the system controlled by valve 48.

Liquid nitrogen (−196° C.) is used to cool traps 16 and 18. Alternate cooling temperatures should be lower than −50° C. The trap temperatures can be varied at the discretion of the analyst technician. The transfer lines and capillary interface are, each, heated to 80° C. The normal temperature ranges should be from 50° C. to 100° C. The transfer line temperatures can certainly be increased or reduced at the discretion of the analyst technician. The precooling trap 18 is normally operated at −20° C. but any temperature between 0° C. and −50° C. is acceptable. This temperature appears to be related to the degree of vacuum supplied by the vacuum pump. The sample bath temperature in flask chamber 10 can vary between −40° C. and 100 C. but the temperature of the bath is preferably between 30° C. to 50° C.

FIG. 2 illustrates in graphical form the results obtained in using vacuum distillation and of fused-silica capillary column (FSCC) chromatography to evaluate peak shapes and for calculating the tailing factors for various volatile organic pollutant compound obtained from analyzing fish samples. As shown in FIG. 2, the intensity in mm. is plotted against retention time in seconds for the various organic compounds subject to FSCC chromatographic analysis to obtain the various peak shapes shown in the figure. The mathematical process for calculating the tailing-factor for a volatile bromoform pollutant is shown in the right-hand side of FIG. 2. The peak height determined to be 72 mm according to the process described in Federal Register, 1979, 44 (No. 233) 69532–69552 is plotted as line DE in the figure. Line BD in FIG. 2 represents 10% of the peak height for bromoform which calculates to 7.2 mm. The line AC shows the peak width at 10% of the peak height which measures 50.2 mm, as shown in FIG. 2. Segments AB and BC of line AC respectively measure 19.2 mm and 31 mm. The tailing factor for bromoform may be calculated from the following formula:

Tailing Factor = BC/AB = 31 mm/19.2 mm = 1.6

Thus, the tailoring factor for bromoform calculates out to a value of 1.6. The scale for measuring the various peak dimensions in millimeters is shown in FIG. 2 and applies to the scale of measurement for the corresponding dimensions in FIGS. 3 to 5, inclusive.

In a manner similar to that set forth above with respect to FIG. 2, the tailoring factor for benzene in FIG. 3 is mathematically calculated, using the foregoing formula, to a value of 1.2.

Similarly, the tailoring factor for vinyl chloride in FIG. 4 is calculated to a value of 1.5 and that of 1,1,2,2 tetrachloroethane in FIG. 5 is calculated to 1.0.

The above tailing factors were calculated by analyzing a solution containing 100 ng each of the volatile organic priority pollutants in a standard analysis distillation, and the tailing factors are listed in Table I below. Tailing factor requirements are not indicated in the Federal Register for volatile organic priority pollutants; however, a comparison can be made for the tailing factor requirement for semivolatile chromatography with 100 ng benzidine (tailing factor to be less than 3) and 40 ng pentachlorophenol (tailing factor to be less than 5). For the VOAs 77% of the tailing factors are less than 1.7. Tailing factors exceeded 3 only for acrolein and acrylonitrile. The tailing factors for late-eluting aromatic pollutants were less than 2 for those evaluated (naphthalene 1.2, 4-ethyl-1, 2-dimethyl benzene 0.9, 1, 3, 5-trimethyl benzene 1.1, indan 1.0, propyl benzene 1.2, and 4-carene 1.3). Symetrical peak shapes are necessary for accurate automatic computerized peak finding and integration.

Table I, below, shows retention time and tailing factor for various volatile organic pollutants including those illustrated in FIG. 2–5.

TABLE I
IDENTIFICATION AND TAILING FACTORS OF VARIOUS VOLATILE ORGANIC POLLUTANTS

| | Compound | Retention Time[1] | Tailing Factor[2] |
|---|---|---|---|
| 1 | chloromethane | 7:54 | 1.5 |
| 2 | vinyl chloride | 8:16 | 1.5 |
| 3 | bromomethane | 8:48 | 1.9 |
| 4 | chloroethane | 8:59 | 2.9 |
| 5 | trichlorofluoromethane | 9:26 | 1.6 |
| 6 | acrolein | 9:31 | 3.8 |
| 7 | acetone | 9:36 | 2.1 |
| 8 | 1,1-dichloroethene | 9:49 | 1.1 |
| 9 | acrylonitrile | 9:55 | 5.9 |
| 10 | dichloromethane | 9:58 | 2.3 |
| 11 | trans-1,2-dichloroethene | 10:17 | 1.3 |
| 12 | 1,1-dichloroethane | 10:26 | 1.6 |
| 13 | bromochloromethane (internal standard) | 10:49 | 2.0 |
| | chloroform | 10:49 | 2.4 |
| 14 | 1,1,1-trichloroethane | 11:08 | 1.0 |
| | 1,2-dichloroethane | 11:10 | 1.5 |
| 15 | d6-benzene (internal standard) | 11:17 | 1.5 |
| | benzene | 11:19 | 1.2 |
| | carbon tetrachloride | 11:19 | 1.1 |
| 16 | trichloroethene | 11:43 | 1.4 |
| | 1,2-dichloropropane | 11:43 | 1.3 |
| 17 | bromodichloromethane | 11:50 | 1.6 |
| 18 | 2-chloroethylvinyl ether | 12:00 | 1.6 |
| 19 | cis-1,3-dichloropropene | 12:10 | 1.4 |
| 20 | trans-1,3-dichloropropene | 12:27 | 1.1 |
| | d8-toluene (internal standard) | 12:28 | 1.3 |
| 21 | toluene | 12:30 | 1.4 |
| 22 | 1,1,2-trichloroethane | 12:33 | 1.3 |
| | 2-bromo-1-chloropropane (internal standard) | | |
| 23 | dibromochloromethane | 12:53 | 1.9 |
| 24 | tetrachloroethene | 12:58 | 1.2 |
| 25 | chlorobenzene | 13:25 | 1.1 |
| 26 | ethylbenzene | 13:35 | 1.1 |
| 27 | p,m-xylene | 13:41 | 1.2 |
| 28 | bromoform | 14:01 | 1.6 |
| 29 | o-xylene | 14:06 | 1.1 |
| 30 | 1,4-dichlorobutane (internal standard) | 14:21 | 1.4 |
| 31 | 1,1,2,2-tetrachloroethane | 14:27 | 1.0 |

[1] 30 m DB5 fused silica capillary column (0.32 mm bore, 1.0 um film thickness) preceded by 18" of ⅛" O.D. stainless steel tubing. Carrier gas helium at 2 mL/min. Temperature program: 3 min isothermal at −99° C., then 30°/min to 70° C., then 20°/min to 180° C. Hold at 180° C. for 10 minutes.

[2] The tailing factors were calculated as illustrated in FIGS. 2 to 5, inclusive.

EXAMPLE

A vacuum distillation apparatus capable of concentrating volatile compounds contained in fish samples will be described below. The vacuum distillate containing the volatile pollutants will be analyzed by gas chromatography/mass spectrometry (GC/MS) by practicing a distillation procedure on 10 gram fish samples using a fused-silica capillary column (FSCC). The volatile organic priority pollutants and additional compounds detected in the volatile distillate will be listed in the various Tables II–VI which follow the detailed precedure described below.

INTRODUCTION

It has been found that volatile organic priority pollutants could be quantitatively concentrated in a cold trap ($-196°$ C.) after vacuum distillation from fish tissue samples (1)[*]. In that study, as well as in other procedures (2,3)[*], packed columns recommended for volatile organic priority pollutants determinations were used (4)[*]. Extended column heating is necessary to remove the volatile organic compounds that slowly elute from the packed columns at the upper temperature limit of the columns. The extended heating period interferes with sequential analysis and severely limits the number of analyses that can be performed in a day.

[*] See list of references which follow below.

This study is an evaluation of a fused-silica capillary column and the chromatography of volatile compounds distilled from fish samples. A vacuum distillation apparatus was constructed to directly transfer the volatile concentrate to a fused-silica capillary column (FSCC) for separation. An additional concern of this work was the identification of compounds that might be determined using the vacuum distillate.

EXPERIMENTAL

Chemicals.

Blank water is prepared by boiling 1 L freshly distilled water down to 900 mL and transferring the water to a 1-liter volumetric flask that was modified by replacing the ground joint fitting with a 15 mm i.d. O-ring connector. The boiled distilled water is degassed by connecting the flask to the vacuum distiller at the sample chamber site (see FIG. 1) and evacuating for 15 minutes while continuously agitating the flask in an ultrasonic cleaner. After evacuation, the flask was sealed with a cap made from an O-ring connector, Buna-N-O-ring, and a pinch clamp.

Bromochloromethane 1-chloro-2-bromopropane and 1,4-dichlorobutane (Supelco Incorporated, Belafonte, Pa.) d6 benzene and d8 toluene (Merck Incorporated, Rahway, N.J.) are used as internal standards. These standards are combined and diluted with methanol to make 2 mg/ml stock solution. An internal standard spike solution is prepared by adding 8 μl of the internal standard stock solution to 1 ml of blank water. Internal standard spikes are added to each sample by injecting 5 μl of the internal standard stock solution (80 ng) to 2 ml blank water contained in a 5 ml gastight luer-tip syringe and adding the syringe contents to the sample.

The volatile priority pollutant standards were obtained from Supelco Incorporated (Belafonte, Pa.). These standards are combined and diluted in ethyleneglycol to make 125 ng/μl standard solution. Standard solutions are prepared by injecting the desired amount of standard compounds to 2 ml blank water containing the internal standard spike.

Apparatus (see FIG. 1).

The vacuum distiller removes volatile organic compounds from samples placed in a sample chamber and the vapors pass through cold trap 18 where water is condensed. Compounds that pass through 18 are condensed in cryogenic trap 16, cooled in liquid nitrogen. After volatile distillation is complete trap 16 slowly warms to room temperature and the vapors recondensed in cryogenic focussing trap 20. Trap 20 is heated to 150° C. and the vapors are flushed with helium carrier gas to the GC/MS. The 6-port valves (36 and 34) direct the transfer of the volatile vapors.

The low pressure used during distillation is supplied by a vacuum pump capable of $10^{-3}$ torr and a 25 L/min flow rate. A glass trap is connected to the $\frac{3}{8}''$ i.d. copper vacuum manifold with 15 mm i.d. O-ring connectors. Cooling the trap in a liquid-nitrogen bath prevents pump oil vapors back flushing to trap 16 and preventing water vapors reaching the vacuum pump.

Transfer lines that connect to the 6-port valves are 1/16″ O.D. stainless steel tubing and are connected with 1/16″ O.D. compression fittings. The other transfer lines are glass-lined stainless steel $\frac{1}{4}''$ O.D. tubing and connections are made with compression fittings and graphite ferrules. Gastight Nupro B-4BKT toggle valves (valves 38–50) are connected to the glass-lined tubing with $\frac{1}{4}''$ O.D. compression fittings and graphite ferrules. Stainless steel Valco 6-port valves (36, 34) are connected with 1/16″ O.D. compression fittings.

The sample chamber 10 consists of a 100 mL pyrex bulb joined to a 15 mm i.d. pyrex O-ring connector. Trap 18 consists of a pyrex cylinder (3.5 cm diameter and 19 cm long) joined to a 15 mm i.d. pyrex O-ring connector. Modified stainless steel fittings, made by silver soldering the necessary stainless steel $\frac{1}{4}''$ O.D. compression fitting bodies to a 15 mm i.d. stainless steel O-ring connector, connect the glass traps with O-ring fittings. The top soldered compression fitting is drilled with a $\frac{1}{4}''$ diameter drill bit which allows the $\frac{1}{4}''$ glass-lined transfer line to extend through the compression fitting/O-ring connector and into the glass traps. Trap 20 is 15 cm of $\frac{1}{8}''$ O.D. quartz tubing bent in a U-shape. Trap 20 is connected to the system with $\frac{1}{8}''$ O.D. compression fittings and graphite ferrules. A variable transformer is used to adjust current to a 30 AWG nichrome wire wrapped around the quartz trap 20 so the trap is heated to 180° C.

A stainless steel box 72 cm long × 10 cm deep × 26 cm high encloses the valves and transfer lines. Heating tape is wrapped around the transfer lines and valves and maintains the temperature of the vacuum distillation apparatus at 80° C. The transfer line between the vacuum distiller and the FSCC is kept at 120° C. A helium line is connected to the vacuum distiller at valve 48 to vary pressure in the system and to check for possible leaks. A mechanical pressure gauge measures pressure (0–1000 mm Hg).

Extracts prepared by the vacuum distiller are analyzed by a Finnigan 1020 GC/MS. A DB5 capillary column (30 m long, 0.32 mm i d., 1.0 um film thickness) obtained from J & W Scientific, Inc. (Rancho Cordova, Ca) was used for chromatography. The gas chromatograph (GC) oven temperature is programmed at $-99°$ C. for three minutes and then increased to 70° C. at a rate of 30° C./min and then to 180° C. at a rate of 20° C./min. The GC temperature program begins as the transfer of the volatile distillate to the GC is started. Helium carrier gas with a flow of 2 mL/min assists transfer. The GC effluent is analyzed by the mass spectrometer set to scan from 46 m/e (mass/electron) to 260 m/e at 1-second intervals.

Procedure.

The fish samples are prepared from fish delivered to the laboratory packed in dry ice. Whole fish are chopped at the laboratory using a food cutter (Hobart, 8145 Model, without attachment hub). Liquid nitrogen is added to the samples during chopping to prevent evaporation of volatile organic compounds. Ten grams of homogenized fish tissue is placed in the sample chamber glassware 10, previously described, and sealed using a Buna-N O-ring, a 15 mm i.d. O-ring connector cap and a pinch clamp. The sealed samples are stored in a freezer until analyzed.

Residual moisture is removed from the vacuum distillation apparatus by opening only valves 38, 40, 44 and 46 and evacuating the sample chamber 10, trap 18, trap 16, and the joining transfer lines. The evacuation is usually continued for 7 minutes after the disappearance of any visible moisture in the glass traps.

Traps 18 and 16 are cooled after residual moisture has been removed from the apparatus. Trap 18 is cooled in a $-20° \pm 1°$ C. ethanol bath contained in a dewar (12 cm wide, 20 cm deep). Trap 16 is cooled with liquid nitrogen ($-196°$ C.), a (dewar, 7 cm wide, 15 cm deep). These temperatures are chosen such that one drop of water condenses in trap 16 during vacuum distillation.

After closing valves 40 and 46 a sample storage vessel 10 (sample chamber) containing a frozen 10 g fish sample is connected to the vacuum distiller and valve 46 is opened. After the sample chamber 10 is connected, the sample spike solution as previously described is added. Analyses of volatile organic priority pollutant standards and analysis of the background are accomplished by analyzing sample spike solutions added to empty sample chambers. The spike solutions are added by attaching the 5 mL syringe to the luer fitting attached to valve 50. Valve 50 is opened and the sample spike solution is pulled into the sample chamber by the vacuum in trap 18, trap 16, and sample chamber. Valve 50 is closed. Valves 38, 44 and 46 are opened and valves 40, 42 and 50 remain closed. Valve 48 is opened to allow helium (5 psi) to enter the sample chamber and adjoining traps 18 and 16 until 360 torr is obtained. The sample chamber 10 is emmersed in a 50° C. water bath contained in a Branosonic 12 ultrasonic cleaner and agitated for 5 minutes. An earlier experiment found that continuous agitation of the water bath contained in the ultrasonic cleaner used warmed the water to approximately 50° C.

Transfer of volatile compounds is begun by opening valve 40 and ultrasonic agitation is continued. The pressures in the sample chamber and trap 18 during vacuum distillation are due to the water vapor pressures ($\sim 93$ torr Hg at 50° C., 0.78 torr Hg at $-20°$ C.) (5).* Vacuum distillation is stopped after 15 minutes by closing valves 40, 44 and 46.
* See list of references which follow below.

The concentrated volatile compounds contained in the trap 16 after completion of the vacuum distillation are transferred to trap 20. Trap 20 is prepared prior to the transfer by turning off the transformer used to heat trap 20 and cooling trap 20 in liquid nitrogen. The 6-port valves are in the transfer position (continuous lines in 6-port valves as illustrated in FIG. 1) and valve 42 is opened. The liquid nitrogen bath is removed from trap 16 and the trap is allowed to warm to ambient temperature. The volatilized distillate is recondensed in trap 20.

After 15 minutes the transfer of the volatile compounds to 20 the 6-port valves 36 and 34 are switched to the injection position (broken lines in 6-port valves, see FIG. 1 of drawing). The GC oven cooled to $-99°$ C. with liquid nitrogen, and temperature programmed as previously described, is started, scanning by the mass spectrometer is begun, and trap 20 is heated to 180° C. The transfer of the concentrate to the capillary column is completed after 3 minutes.

During the distillate transfer (trap 16 to trap 20) the apparatus is prepared for the next sample distillation. The sample chamber and trap 18 are replaced with clean and dry units. The sample spike inlet is flushed with helium (5 psi) by opening and then closing valves 48 and 50.

During the GC injection of the distillate, trap 18, trap 16, and the sample chamber are evacuated by opening valves 40, 44 and 46 and closing valve 42. After the 3-minute transfer of the distillate to the fused-silica capillary column, the 6-port valves (36 and 34) are returned to the transfer position and trap 20 is evacuated to remove any remaining volatile compounds. The next sample can then be introduced and distillation of volatile compounds begun.

The volatile concentrate is analyzed by GC/MS using the parameters previously described. Compounds are manually selected from the resulting reconstructed ion chromatogram and the compound is identified by computerized forward-searching the EPA/NIH mass spectral library. Many isomers cannot be distinguished by mass spectra and therefore the best matching library spectrum is used as identification. When identification was not possible the best general structute and chemical formula are listed.

RESULTS AND DISCUSSION

The use of vacuum distillation and FSCC chromatography has greatly improved the chromatography of volatile organic compounds from fish samples. Superior recoveries of the volatile organic priority pollutant compounds have been shown to be attained with vacuum distillation (1)*, and with FSCC late-eluting compounds are rapidly eluted by elevating the column temperature to 180° C.
* See list of references which follow below.

Table II, below, lists the identification of various voltatile organic pollutants by determining the molecular weight of the pollutant and its retention time from a chromatogram of a vacuum distillate prepared from a 10 gram sample of rainbow trout.

TABLE II

IDENTIFICATION OF VARIOUS VOLATILE ORGANIC POLLUTANTS IN A RAINBOW TROUT SAMPLE

| | Formula | Retention Time[1] | Molecular Weight | Identification[2] |
|---|---|---|---|---|
| 1 | $CCl_2F_2$ | 7:08 | 120 | dichlorodifluoromethane |
| 2 | $CH_3Cl$ | 7:42 | 50 | chloromethane |
| 3 | $C_4H_8$ | 8:11 | 56 | 2-methyl-1-propene |
| 4 | $C_4H_6$ | 8:18 | 54 | 1,3-butadiene |
| 5 | $C_3H_6O$ | 9:31 | 58 | propanal |
| 6 | $CH_2Cl_2$ | 10:00 | 84 | dichloromethane |
| 7 | $C_3H_6O$ | 10:04 | 58 | propanal |
| 8 | $C_6H_{14}$ | 10:27 | 86 | 3-methylpentane |
| 9 | $C_5H_{10}O$ | 10:37 | 86 | 2-methylbutanal |
| 10 | $C_5H_6O$ | 10:44 | 82 | 2-methylfuran |
| 11 | $CH_2ClBr$ | 10:54 | 128 | bromochloromethane |
| 12 | $C_6H_{12}$ | 11:00 | 84 | 2-methyl-1-pentene |
| 13 | $C_2H_3Cl_3$ | 11:14 | 132 | 1,1,1-trichloroethene |
| 14 | $C_6D_6$ | 11:25 | 84 | d6-benzene |
| | $C_6H_6$ | 11:27 | 78 | benzene |
| 15 | $C_7H_{16}$ | 11:31 | 100 | 3-methylhexane |
| 16 | $C_4H_8O$ | 11:47 | 72 | 3-buten-2-ol |
| 17 | $C_7H_{14}$ | 12:11 | 98 | methylcyclohexane |
| 18 | $C_7H_{14}$ | 12:17 | 98 | ethylcyclopentane |
| 19 | $C_5H_8O$ | 12:31 | 84 | 2,3-dihydro-4-methylfuran |
| 20 | $C_7D_8$ | 12:38 | 100 | d8-toluene |
| | $C_7H_8$ | 12:41 | 92 | toluene |
| 21 | $C_6H_{12}O$ | 12:50 | 100 | 1,3-dimethylcyclohexane |
| 22 | $C_6H_{12}O$ | 13:03 | 100 | 2-methylcyclopentanol |
| | $C_8H_{14}$ | 13:11 | 110 | 3-methyl-1,4-heptadiene |
| 23 | $C_2Cl_4$ | 13:15 | 164 | tetrachloroethene |
| | $C_8H_{14}$ | 13:17 | 110 | 3-methyl-1,4-heptadiene |
| 24 | $C_9H_{18}$ | 13:31 | 126 | 1,2,4-trimethylcyclohexane |
| 25 | $C_8H_{16}$ | 13:34 | 112 | ethylcyclohexane |
| 26 | $C_5H_{10}N_2$ | 13:48 | 98 | 4,5-dihydro-2,4-dimethylimidazole |

TABLE II-continued
IDENTIFICATION OF VARIOUS VOLATILE ORGANIC POLLUTANTS IN A RAINBOW TROUT SAMPLE

| | Formula | Retention Time[1] | Molecular Weight | Identification[2] |
|---|---|---|---|---|
| 27 | $C_8H_{10}$ | 14:02 | 106 | ethylbenzene |
| 28 | $C_8H_{10}$ | 14:12 | 106 | xylene |
| 29 | $C_9H_{18}$ | 14:22 | 126 | 1,2,4-trimethylcyclohexane |
| 30 | $C_9H_{16}O$ | 14:30 | 140 | 8-nonen-2-one |
| 31 | $C_9H_{20}$ | 14:38 | 128 | nonane |
| 32 | $C_8H_{10}$ | 14:43 | 106 | o-xylene |
| 33 | $C_4H_8Cl_2$ | 14:58 | 126 | 1,4-dichlorobutane |
| 34 | $C_9H_{12}$ | 15:20 | 120 | (1-methylethyl)benzene |
| 35 | $C_9H_{18}$ | 15:28 | 126 | propylcyclohexane |
| 36 | $C_{10}H_{16}$ | 15:34 | 136 | 4-carene |
| 37 | $C_9H_{12}$ | 15:55 | 120 | propylbenzene |
| 38 | $C_9H_{12}$ | 16:05 | 120 | 1-ethyl-3-methylbenzene |
| 39 | $C_9H_{12}$ | 16:12 | 120 | 1,3,5-trimethylbenzene |
| 40 | $C_9H_{12}$ | 16:28 | 120 | 1-ethyl-4-methylbenzene |
| 41 | $C_9H_{12}$ | 16:44 | 120 | 1,3,5-trimethylbenzene |
| 42 | $C_{10}H_{14}$ | 17:00 | 134 | (2-methylpropyl)benzene |
| 43 | $C_{10}H_4$ | 17:04 | 134 | (1-methylpropyl)benzene |
| 44 | $C_{10}H_{14}$ | 17:12 | 134 | 1-methyl-3-propylbenzene |
| 45 | $C_9H_{12}$ | 17:19 | 120 | 1,2,3-trimethylbenzene |
| 46 | $C_9H_{10}$ | 17:38 | 118 | indan |
| 47 | $C_{10}H_{14}$ | 17:47 | 134 | 1-methyl-4-propylbenzene |
| 48 | $C_{10}H_{14}$ | 17:53 | 134 | 2-ethyl-1,4-dimethylbenzene |
| 49 | $C_7H_{10}O$ | 18:01 | 110 | 2,2-dimethyl-3,4-pentadienal |
| 50 | $C_{10}H_{14}$ | 18:07 | 134 | 1-methyl-4-propylbenzene |
| 51 | $C_{10}H_{14}$ | 18:16 | 134 | 2-ethyl-1,2-dimethylbenzene |
| 52 | $C_{10}H_{14}$ | 18:26 | 134 | 4-ethyl-1,2-dimethylbenzene |
| 53 | $C_{10}H_{12}$ | 18:33 | 132 | 1-methylindan |
| 54 | $C_{10}H_{14}$ | 18:51 | 134 | 1-ethyl-3,5-dimethylbenzene |
| 55 | $C_{10}H_{14}$ | 19:00 | 134 | 1,2,3,5-tetramethylbenzene |
| 56 | $C_{10}H_{14}$ | 19:06 | 134 | 1,2,4,5-tetramethylbenzene |
| 57 | $C_{11}H_{16}$ | 19:23 | 148 | (1-ethylpropyl)benzene |
| 58 | $C_{10}H_{12}$ | 19:30 | 132 | 4-methylindan |
| 59 | $C_{10}H_{12}$ | 19:42 | 132 | 1-methylindan |
| 60 | $C_{11}H_{16}$ | 19:51 | 148 | p-isobutyltoluene |
| 61 | $C_{10}H_{12}$ | 19:58 | 132 | 1,2,3,4-tetrahydronaphthalene |
| 62 | $C_{11}H_{16}$ | 20:12 | 148 | 1-ethyl-3-(1-methylethyl)benzene |
| 63 | $C_{11}H_{14}$ | 20:17 | 146 | 1,1-dimethylindan |
| 64 | $C_{10}H_{18}$ | 20:23 | 128 | naphthalene |
| | $C_{10}H_{12}O$ | 20:23 | 148 | 1-(4-ethylphenyl)ethanone |
| 65 | $C_{11}H_{16}$ | 20:35 | 148 | ethyl-1,2,4-trimethylbenzene |
| 66 | $C_{12}H_{18}$ | 20:45 | 162 | p-(1-ethylproply)toluene |

[1] 30 m DB5 fused silica capillary column (0.32 mm bore, 1.0 m film thickness) preceded by 18" of ¼"O.D. stainless steel tubing. Carrier gas helium at 2 mL/min. Temperature program: 3 min isothermal at −99° C., then 30°/minto 70° C., then 20°/min to 180° C. Hold at 180° C. for 10 minutes.
[2] Identifications were made by computerized search of the EPA/NIH mass spectral library.

Table III, below, lists the identification of a number of volatile organic pollutants by evaluating data obtained from a chromatogram of a vacuum distillate prepared from a 10 gram large mouth Bass sample spiked with 100 mg of each of the volatile priority pollutants.

TABLE III
IDENTIFICATION OF VARIOUS VOLATILE ORGANIC POLLUTANTS IN A LARGE MOUTH BASS SAMPLE

| | Formula | Retention Time[1] | Molecular Weight | Identification[2] |
|---|---|---|---|---|
| 1 | $CH_3Cl$ | 7:45 | 50 | chloromethane |
| 2 | $C_2H_3Cl$ | 8:12 | 62 | vinylchloride |
| 3 | $C_4H_8$ | 8:18 | 56 | 2-butene |
| 4 | $C_4H_6$ | 8:23 | 54 | 1,3-butadiene |
| 5 | $C_4H_8$ | 8:32 | 56 | 2-butene |
| 6 | $C_4H_4$ | 8:38 | 52 | 1-buten-3-yne |
| 7 | $CH_3Br$ | 8:46 | 94 | bromomethane |
| 8 | $C_2H_5Cl$ | 8:58 | 64 | chloroethane |
| 9 | $C_3H_9N$ | 9:15 | 59 | N,N—dimthylmethanamine |
| 10 | $CCl_3F$ | 9:24 | 136 | trichlorofluoromethane |

TABLE III-continued
IDENTIFICATION OF VARIOUS VOLATILE ORGANIC POLLUTANTS IN A LARGE MOUTH BASS SAMPLE

| | Formula | Retention Time[1] | Molecular Weight | Identification[2] |
|---|---|---|---|---|
| | $C_5H_{10}$ | 9:27 | 70 | 1,1-dimethylcycloprpopane |
| 11 | $C_4H_8O$ | 9:32 | 72 | 2-buten-1-ol |
| 12 | $C_5H_{10}$ | 9:39 | 70 | 2-methyl-2-butene |
| 13 | $C_2H_2Cl_2$ | 9:46 | 96 | 1,1-dichloroethene |
| | $CH_3I$ | 9:47 | 142 | iodomethane |
| 14 | $C_3H_3N$ | 9:50 | 53 | acrylonitrile |
| | $C_5H_8$ | 9:50 | 68 | cyclopentene |
| 15 | $CH_2Cl_2$ | 9:55 | 84 | dichloromethane |
| | $C_5H_6$ | 9:58 | 66 | 1,3-cyclopentadiene |
| 16 | $C_2H_2Cl_2$ | 10:13 | 96 | trans-1,2-dichloroethene |
| 17 | $C_2H_4Cl_2$ | 10:21 | 98 | 1,1-dichloroethane |
| 18 | $C_5H_{10}O$ | 10:30 | 86 | 2-methylbutanal |
| 19 | $C_5H_6O$ | 10:34 | 82 | 2-methylfuran |
| 20 | $CH_2ClBr$ | 10:42 | 128 | bromochloromethane |
| | $CHCl_3$ | 10:42 | 118 | trichloromethane |
| 21 | $C_3H_6O$ | 10:35 | 58 | propanal |
| 22 | $C_2H_3Cl_3$ | 10:58 | 132 | 1,1,1-trichloroethane |
| | $C_2H_4Cl_2$ | 11:00 | 98 | 1,2-dichloroethane |
| 23 | $C_6D_6$ | 11:08 | 84 | d$_6$-benzene |
| | $C_6H_6$ | 11:09 | 78 | benzene |
| | $CCl_4$ | 11:09 | 152 | carbon tetrachloride |
| 24 | $C_2HCl_3$ | 11:29 | 130 | trichloroethane |
| | | 11:30 | 112 | 1,2-dichloropropane |
| 25 | $CHCl_2Br$ | 11:34 | 162 | bromodichloromethane |
| 26 | $C_3H_7I$ | 11:40 | 170 | 2-iodopropane |
| 27 | $C_4H_7OCl$ | 11:45 | 106 | 2-chloroethylvinyl ether |
| 28 | $C_3H_4Cl_2$ | 11:51 | 110 | cis-1,3-dichloropropene |
| 29 | $C_4H_8O$ | 11:57 | 72 | 3-buten-2-ol |
| 30 | $C_7D_8$ | 12:07 | 100 | d$_8$-toluene |
| | $C_3H_4Cl_2$ | 12:07 | 110 | trans-1,3-dichloropropene |
| 31 | $C_7H_8$ | 12:09 | 92 | toluene |
| | $C_2H_3Cl_3$ | 12:11 | 132 | 1,1,2-trichloroethane |
| 32 | $C_3H_6ClBr$ | 12:15 | 156 | 2-bromo-1-chloropropane |
| 33 | $CHClBr_2$ | 12:28 | 206 | dibromochloromethane |
| 34 | $C_6H_{12}O$ | 12:33 | 100 | 2-methylcyclopentanol |
| 35 | $C_2Cl_4$ | 12:37 | 164 | tetrachloroethene |
| 36 | $C_6H_5Cl$ | 13:00 | 112 | chlorobenzene |
| 37 | $C_8H_{10}$ | 13:09 | 106 | ethylbenzene |
| 38 | $C_8H_{10}$ | 13:13 | 106 | m,p-xylene |
| 39 | $C_8H_{16}O$ | 13:19 | 128 | 2-methyl-1,4-heptanone |
| 40 | $CHBr_3$ | 13:26 | 250 | bromoform |
| 41 | $C_8H_{10}$ | 13:30 | 106 | o-xylene |
| 42 | $C_7H_{14}O$ | 13:33 | 114 | 4-methylcyclohexanol |
| 43 | $C_4H_8Cl_2$ | 13:37 | 126 | 1,4-dichlorobutane |
| 44 | $C_2H_2Cl_4$ | 13:41 | 166 | 1,1,2,2-tetrachloroethane |

[1] m DB5 fused silica capillary column (0.32 mm bore, 1.0 m film thickness) preceded by 18" of ¼" O.D. stainless steel tubing. Carrier gas helium at 2 mL/min. Temperature program: 3 min isothermal at −99 C., then 30°/min to 70° C., then 20°/min to 180° C. Hold at 180° C. for 10 minutes.
[2] Identifications wera made by computerized search of the EPA/NIH mass spectral library.

Table IV, below, lists the identification of various volatile organic pollutants by evaluation of data obtained from a chromatogram of a vacuum distillate prepared from a 10 gram carp sample.

TABLE IV
IDENTIFICATION OF VARIOUS VOLATILE ORGANIC POLLUTANTS IN CARP SAMPLE

| | Formula | Retention Time[1] | Molecular Weight | Identification[2] |
|---|---|---|---|---|
| 1 | $C_4H_8$ | 8:26 | 56 | 2-butene |
| 2 | $C_4H_6$ | 8:31 | 54 | 1,3-butadiene |
| 3 | $C_4H_8O$ | 9:23 | 72 | 2-methyl-2-propen-1-ol |
| 4 | $C_4H_8O$ | 9:39 | 72 | 2-buten-1-ol |
| 5 | $C_5H_8$ | 9:44 | 68 | 3-methyl-1,2-butadiene |
| 6 | $C_5H_6$ | 10:07 | 66 | 1,3-cyclopentadiene |
| 7 | $CH_2Cl_2$ | 10:15 | 84 | dichloromethane |
| 8 | $C_5H_{10}O$ | 10:24 | 86 | 1-methoxy-1-butene |
| 9 | $C_6H_{14}$ | 10:34 | 86 | 3-methylpentane |
| 10 | $C_6H_{14}$ | 10:45 | 86 | 3-methylpentane |

TABLE IV-continued
IDENTIFICATION OF VARIOUS VOLATILE ORGANIC POLLUTANTS IN CARP SAMPLE

| | Formula | Retention Time[1] | Molecular Weight | Identification[2] |
|---|---|---|---|---|
| 11 | $C_6H_{14}O$ | 11:07 | 102 | 3-methyl-1-pentanol |
| 12 | $C_6H_{10}$ | 11:22 | 82 | (1-methylethenyl)-cyclopropane |
| 13 | $C_6D_6$ | 11:30 | 84 | $d_6$-benzene |
| | $C_6D_6$ | 11:31 | 78 | benzene |
| 14 | $C_7H_{14}$ | 11:45 | 98 | 1,3-dimethylcyclopentane |
| 15 | $C_7H_{14}O$ | 11:51 | 114 | 4-methylcyclohexanol |
| 16 | $C_7H_{12}$ | 11:59 | 96 | 1,4-dimethyl-1,2-pentadiene- |
| 17 | $C_7H_{14}$ | 12:08 | 98 | methylcyclohexane |
| 18 | $C_7H_{14}$ | 12:13 | 98 | ethylcyclopentane |
| 19 | $C_8H_{18}$ | 12:27 | 114 | 3,3-dimethylhexane |
| 20 | $C_7D_8$ | 12:35 | 100 | $d_8$-toluene |
| | $C_7H_8$ | 12:36 | 92 | toluene |
| 21 | $C_8H_{16}$ | 12:41 | 112 | 1,2-dimethylcyclohexane |
| 22 | $C_6H_{12}O$ | 12:57 | 100 | 2-methylcyclopentanol |
| 23 | $C_9H_{18}$ | 13:13 | 126 | 1,2,4-trimethylcyclohexane |
| 24 | $C_9H_{18}$ | 13:26 | 126 | 1,1,2-trimethylcyclohexane |
| 25 | $C_8H_{10}$ | 13:36 | 106 | m,p-xylene |
| 26 | $C_8H_{10}$ | 13:54 | 106 | o-xylene |
| 27 | $C_8H_{18}$ | 14:01 | 126 | 1-ethyl-1-methylcyclohexane |
| 28 | $C_9H_{16}$ | 14:13 | 124 | indan |
| 29 | $C_{10}H_{16}$ | 14:24 | 136 | 4-carene |
| 30 | $C_9H_{12}$ | 14:40 | 120 | propylbenzene |
| 31 | $C_9H_{12}$ | 14:47 | 120 | 1-ethyl-3-methylbenzene |
| 32 | $C_9H_{12}$ | 14:54 | 120 | 1,3,5-trimethylbenzene |
| 33 | $C_9H_{12}$ | 15:05 | 120 | 1,2,4-trimethylbenzene |
| 34 | $C_9H_{12}$ | 15:20 | 120 | 1,2,3-trimethylbenzene |
| 35 | $C_9H_{10}$ | 15:34 | 134 | methylbenzeneacetaldehyde |
| 36 | $C_{10}H_{16}$ | 15:54 | 136 | 1-methyl-4-(1-methylethenyl)cyclohexene |
| 37 | $C_9H_{10}$ | 16:09 | 118 | 1-ethenyl-2-methylbenzene |
| 38 | $C_{10}H_{14}$ | 16:21 | 134 | 1,2-diethylbenzene |
| 39 | $C_{10}H_{14}$ | 16:31 | 134 | 1-ethyl-2,3-dimethylbenzene |
| 40 | $C_{10}H_{18}$ | 16:37 | 138 | decalin |
| 41 | $C_{10}H_{14}$ | 16:42 | 134 | (1-methylpropyl)benzene |
| 42 | $C_{10}H_{14}$ | 16:53 | 134 | 1,4-diethylbenzene |
| 43 | $C_9H_{10}O$ | 17:04 | 134 | 2,5-dimethylbenzaldelhyde |
| 44 | $C_{10}H_{12}$ | 17:10 | 132 | 2-methylindan |
| 45 | $C_{11}H_{16}$ | 17:18 | 148 | p-isobutyltoluene |
| 46 | $C_{10}H_{14}$ | 17:28 | 134 | 1,3-diethylbenzene |
| 47 | $C_{11}H_{20}$ | 17:42 | 152 | 2-methyldecalin |
| 48 | $C_9H_{10}O$ | 17:45 | 134 | 3,4-dimethylbenzaldehyde |
| 49 | $C_{11}H_{14}$ | 17:53 | 146 | 1,6-dimethylindan |
| 50 | $C_{11}H_{20}$ | 18:00 | 152 | 2-methyldecalin |
| 51 | $C_{11}H_{16}$ | 18:14 | 148 | p-isobutyltoluene |
| 52 | $C_{10}H_{12}$ | 18:22 | 132 | 5-methylindan |
| 53 | $C_{11}H_{16}$ | 18:33 | 148 | diethylmethylbenzene |
| 54 | $C_{11}H_{16}$ | 18:39 | 148 | (1,1-dimethylpropyl)benzene |
| 55 | $C_{12}H_{18}$ | 18:53 | 162 | p-(1-ethylpropyl)toluene |
| 56 | $C_{11}H_{14}$ | 18:57 | 146 | 1,1-dimethylindan |
| 57 | $C_{11}H_{16}$ | 19:04 | 148 | 1-ethyl-3-(1-methylethyl)-benzene |
| 58 | $C_{11}H_{16}$ | 19:16 | 148 | 1-ethyl-2,4,5-trimenthylbenzene |
| 59 | $C_{12}H_{18}$ | 19:28 | 162 | 2,4-dimethyl-1-(1-methylpropyl)benzene |
| 60 | $C_{12}H_{22}$ | 19:42 | 166 | 2,6-dimethyldecalin |
| 61 | $C_{12}H_{16}$ | 19:52 | 160 | 1,4,7-trimethylindan |
| 62 | $C_{11}H_{14}$ | 20:02 | 146 | (3-methyl-2-butenyl)-benzene |
| 63 | $C_{11}H_{14}$ | 20:18 | 146 | 5,6-dimethylindan |
| 64 | $C_{12}H_{18}$ | 20:28 | 162 | 1,3,5-triethylbenzene |
| 65 | $C_{11}H_{14}$ | 20:39 | 146 | 4,6-dimethylindan |
| 66 | $C_{12}H_{16}$ | 20:45 | 160 | 1,4,7-trimethylindan |
| 67 | $C_{11}H_{10}$ | 20:57 | 142 | 2-methylnaphthalene |

[1] 30 m DB5 fused silica capillary column (0.32 mm bore, 1.0 m film thickness) preceded by 18" of ⅛" O.D. stainless steel tubing. Carrier gas helium at 2 mL/min. Temperature program: 3 min isothermal at −99° C., then 30°/min to 70° C., then 20°/min to 180° C. Hold at 180° C. for 10 minutes.
[2] Identifications were made by a computerized search of the EPA/NIH mass spectral library.

Table V, below, lists retention times and standard deviations for a number of internal standards concentrated by vacuum distillation using a fused silica capillary column.

TABLE V
FUSED SILICA CAPILLARY COLIN RETENTION TIMES FOR INTERNAL STANDARDS CONCENTRATED BY VACUUM DISTILLATION

| Formula | Retention Time[1] | 1σ Standard Deviation[2] | Window Width (2σ Standard Deviation)[2] |
|---|---|---|---|
| bromochloromethane | 10:52 | 20 Seconds | 40 Seconds |
| $d_6$-benzene | 11:14 | 26 Seconds | 52 Seconds |
| $d_8$-toluene | 12:29 | 28 Seconds | 56 Seconds |
| 2-bromo-1-chloropropane | 12:38 | 30 Seconds | 60 Seconds |
| 1,4-dichlorobutane | 14:10 | 66 Seconds | 132 Seconds |

[1] m DB5 fused silica capillary column (0.32 mm bore, 1.0 m film thickness) preceded by 18" of ⅛" O.D. stainless steel tubing. Carrier gas helium at 2 mL/min. Temperature program: 3 min isothermal at −99° C., then 30°/minto 70° C., then 20°/min to 180° C. Hold at 180° C. for 10 minutes.
[2] Standard deviations were computed using retention times of the compounds for 8 analysis (3 standard solution distillates, 2 background distillates, and 3 fish distillates.

Table VI, below, lists the vapor pressures in Torr units for a number of identified vacuum distillates of volatile organics.

TABLE VI
VAPOR PRESSURES[1] OF IDENTIFIED VACUUM DISTILLED COMPOUNDS

| | Vapor Pressure in Torrs | | |
|---|---|---|---|
| Compounds | −20° C. | +20° C. | +50° C. |
| Acrylonitrile | 9.830 | 84.89 | 301.2 |
| benzene | 6.28 | 57.36 | 210.3 |
| chlorobenzene | 0.601 | 9.03 | 38.35 |
| chloromethane | 801.5 | 3449 | 8,128 |
| 1,4-diethylbenzene | NC[2] | 1.106 | 6.141 |
| 1,4-diethylbenzene | NC | 1.106 | 6.14 |
| ethyl benzene | 1.21[3] | 7.47 | 32.92 |
| glycol $H_2C-CH_2$ | NC | NC | 0.976[4] |
| isopropyl benzene | NC | 3.345 | 17.4 |
| naphthalene | NC | .053 | .805 |
| n-heptane | 3.34 | 32.75 | 125.2 |
| tetrachlorocthene | 1.11 | 13.65 | 59.60 |
| 1,1,2,2-tetrachloroethane | NC | 4.75 | 23.12 |
| toluene | 2.037 | 20.92 | 82.21 |
| trans-1,2-dimethylcyclohexane | 1.19 | 14.05 | 59.95 |
| 1,3,5-triethylbenzene | NC | NC | 3.38 |
| 1,3,5-triethyl-2-ethyl | NC | NC | 2.00 |
| water | .776 | 17.535 | 92.51 |

[1] Vapor pressures are derived from tables in CRC Handbook of Chemistry and Physics 1972.
[2] Could not be calculated from tables.
[3] Calculated for −10° C.
[4] Calculated for 53° C.

List of numbered references in preceding description follows:

REFERENCES

1. M. H. Hiatt, Anal. Chem 53 (1981) 1541–1543.
2. D. M. Easley, R. D. Kleopfer, A. M. Carasea, J. Assoc. Off. Anal. Chem 64(3) (1981) 653–6.
3. J. Blazevich, U.S. Environmental Protection Agency, Region 10, Manchester, WA. Personal Communication, 1980.
4. Fed. Register, 1979, 44 (No. 233), 69532–69552.
5. Handbook of Chemistry and Physics, CRC Press, 53rd Ed. (1972), D147–D148.
6. U.S. Environmental Protection Agency. "Sampling and Analysis Procedures for Screening of Fish for Priority Pollutants", U.S. Environmental Monitoring and Support Laboratory—Cincinnati. Cincinnati, OH. August 1977.

FURTHER DISCUSSION OF ABOVE RESULTS

The volatile component chromatography of a typical fish sample using a vacuum distillate which was obtained from a 10 g sample of rainbow trout caught on the Colorado River below Hoover Dam is demonstrated in the data shown in Tabe II.

The presence of the volatile organic priority pollutant compounds in a volatile fish distillate is demostrated in the data shown in Table III based on a total ion chromatogram of a vacuum distillate obtained from a 10 g sample of a large mouth bass caught in the San Joaquin River (CA). The 10 g sample was spiked with volatile priority pollutant compounds to 10 ppb. Principle ion mass chromatogram of the VOAs that co-elute with major contaminants may be obtained for propanal and 3-buten-2-ol to demonstrate mass resolution.

The data shown in Table IV is based on a total ion abnormally complex chromatogram of a vacuum distillate obtained from a 10 g aliquot of carp caught in Las Vegas Wash (Nevada), and the major peaks for the various pollutants are listed in Table IV.

Average ratention time, $1\sigma$ deviation and window width $(2\sigma)$ for each of the internal standards is shown in Table V. The results were obtained by sveraging the retention times of the compounds in seven analysis (2 standard, 2 blank and 3 fish analysis).

The vacuum distillation technique is rapid (35 min), and analyses are done in succession at 45 min intervals. This provides an ample time (10 min) for preparation of the vacuum distiller. The sample storage vessels, which also serve as sample distillation chambers, simplify analyses. Samples are easily put into the vessels; the samples are sealed with pinch clamps for storage and directly connected to the apparatus for distillation. Surrogate compounds should be directly added to the samples in the sample chambers before they are stored.

A multitude of organic compounds are detected in the vacuum distillate as characterized in Tables II and IV. The lowest pressures obtained in the distillation apparatus are limited to the vapor pressure of water at $-20°$ C. (the temperature of the water condensation trap 18) which is 0.78 torr (5). Therefore one physical characteristic of compounds that can be completely recovered is the vapor pressure of the compounds be greater than 0.78 torr at $-20°$ C.

An observed physical characteristic of compounds that were detected appears to be the vapor pressure of the compound are typically greater than 0.78 torr at the sample chamber (50° C). This limitation is borne out by comparing identified compounds and their respective vapor pressures at 50° C. (see Table VI). It is interesting to note that naphthalene, a semivolatile priority pollutant, is detected (Table II). The detection of naphthalene is important because naphthalene is a semivolatile priority pollutant presently prepared for determination with liquid extraction concentration (6)*. Liquid extraction obtains a final concentrate that represents an initial 20 g fish sample. Only 2 ul of the extract solution, which represents 40 mg of sample, can be injected onto a capillary column. When the 40 mg sample-equivalent-injection amount is compared to the 10 g sample-equivalent-injection amount as obtained by vacuum distillation it is apparent that the vacuum distillation precedure can be 250 times more sensitive for many semivolatile priority pollutant determinations.

*Reference 6, supra

From the foregoing description a number of advantageous results inherent in the novel VECCCI system of the invention herein are evident. Specifically, (1) There is minimal water vapor present with the final extract which minimizes water interference with the analysis.

(2) The invention works with a minimum of carrier gas, therefore, it is not necessary to remove large quantities of carrier gas. This results in increased sensitivity at lowered cost.

(3) Volatile compounds are isolated without solvents.

(4) Compounds more volatile than water are separated from compounds as volatile or less volatile than water. Any semivolatiles that are trapped with the water in the precooling trap can be determined separately, if desired.

(5) The volatile compounds are totally recovered which eliminates losses experienced with standard extraction procedures. The analysis for volatiles may be conducted using a capillary column for enhanced chromatographic resolution and increased sensitivity.

(6) Volatile compounds are reproducibly desorbed from a wide variety of sample matrices with a minimum of matrix dependence.

(7) Volatile compounds are collected in a trap independent of the analytical method to be used later.

(8) The semivolatiles which have been partially removed from the sample by this procedure are separated from the volatile compounds and analyzed separately.

(9) Capillary interface allows one sample to be transferred to the analytical device while a second sample is being extracted simultaneously.

(10) The VECCCI system can be readily applied to the analysis of matrices, other than water, such as solid matrices and introduces an advantageous means for transferring the volatile components from the sample matrix to the vapor phase.

(11) The VECCCI system will permit precise environmental determinations of volatile organic and inorganic pollutants at detection levels not attainable with the present methods of the known prior art, without an increase in analysis time or in expense compared to such methods of the prior art.

The foregoing description of the specific embodiments will so fully reveal the general nature of the invention that others of ordinary skill in the art can by applying current knowledge, readily modify and/or adapt for various applications such specific embodiments without departing from the generic concept, and therefore, such adaptations and modifications should and are intended to be comprehended within the meaning and range of equivalents of the disclosed embodiments. It is understood that the phraseology or terminology employed herein is used for the purpose of description and not of limitation.

I claim:

1. An apparatus including a vacuum distillation extractor in combination with a cryogenic concentrator which is interfaced by capillary column means to a physico-chemical analytical device for qualitatively and/or quantitatively analyzing volatile or purgeable substances contained in environmental sample matrices, said apparatus comprising a sample chamber provided with an outlet containing said environmental sample, a leak detecting inert gas inlet port, a vacuum pump connected to a vacuum inlet port, a precooling trap, cryogenic concentration trap and cryogenic focusing trap, each of said traps being selectively interconnected with one another and with said leak detecting inert gas inlet port, said vacuum port and said sample chamber outlet by means of a plurality of conduit transfer lines, fluid passage through said transfer lines being controlled by means of a series of selectively actuated valves positioned at various points in said transfer lines, a 6-port valve controlled carrier gas inlet line and a 6-port valve controlled carrier gas and volatile extract outlet line in selective fluid communication with the outlet port from said cryogenic focusing trap, means to selectively heat each of said traps, and capillary column means interfacing gas chromatograph means for analytically determining the composition and concentration of sample pollutants in the volatile extract emanating from the heated cryogen focusing trap.

2. An apparatus as claimed in claim 1 further including a pump oil trap in selective communication with said vacuum port means, a water sample internal standards inlet in selective fluid communication with the outlet of said sample chamber and a vacuum pressure gauge in fluid communication with the outlet of said sample chamber.

3. An apparatus as claimed in either claim 1 or 2, wherein said gas chromotographic determining means comprises a gas chromatograph/mass spectrometer analytical device.

4. An apparatus as claimed in either claim 1 or 2 wherein the valve are automatically actuated by programmable solenoid means.

5. An apparatus as claimed in either claim 1 or 2, further including temperature controllers to maintain proper desired temperatures in the sample chamber and the various cooling traps.

6. An apparatus as cliamed in claim 1 wherein said capillary column means comprises a fused silica capillary column.

* * * * *